US00PP22288P2

(12) United States Plant Patent
Giesen

(10) Patent No.: US PP22,288 P2
(45) Date of Patent: Nov. 29, 2011

(54) *SOLENOSTEMON* PLANT NAMED 'MOS BURVET'

(50) Latin Name: *Solenostemon scutellarioides*
Varietal Denomination: Mos Burvet

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,760

(22) Filed: Jul. 6, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Annette Para
(74) *Attorney, Agent, or Firm* — S. Matthew Edwards

(57) ABSTRACT

A new *Solenostemon* plant named 'Mos Burvet' particularly distinguished by the yellow-green and medium greyed-purple colored foliage, with an upright, well branched and uniform plant habit.

1 Drawing Sheet

Latin name of the genus and species of the plant claimed: *Solenostemon scutellarioides.*

Varietal denomination: 'Mos Burvet'.

BACKGROUND OF THE NEW PLANT

The present invention comprises a new *Solenostemon*, botanically known as *Solenostemon scutellarioides*, and hereinafter referred to by the variety name 'Mos Burvet'.

'Mos Burvet' is a product of a planned breeding program. The new cultivar has yellow-green and medium greyed-purple colored foliage, with an upright, well branched and uniform plant habit.

'Mos Burvet' originated from a hybridization made in January 2006 in a controlled breeding environment in Andijk, Netherlands. The female parent was the unpatented, proprietary plant designated 'CS06-16-1' with smaller and fewer leaves, less branching and thinner stems.

The male parent of 'Mos Burvet' was the unpatented, proprietary plant designated 'CS06-1-1' with smaller leaves, and thinner stems. The resultant seed was sown in July 2006.

'Mos Burvet' was selected as one plant within the progeny of the stated cross in September 2006 in a controlled environment in Andijk, Netherlands.

The first act of asexual reproduction of 'Mos Burvet' was accomplished when vegetative cuttings were propagated from the initial selection in September 2006 in a controlled environment in Andijk, Netherlands.

BRIEF SUMMARY OF INVENTION

Horticultural examination of plants grown from cuttings of the plant initiated in September, 2006, and continuing thereafter, has demonstrated that the combination of characteristics as herein disclosed for 'Mos Burvet' are firmly fixed and are retained through successive generations of asexual reproduction.

'Mos Burvet' has not been observed under all possible environmental conditions. The phenotype may vary significantly with variations in environment such as temperature, light intensity and day length.

Plant Breeders' Rights for this cultivar were applied for in Canada on Feb. 18, 2010 (#10-6842) and in Switzerland on Apr. 15, 2010 (#10-2641). 'Mos Burvet' has not been made publicly available more than one year prior to the filing of this application.

The following traits have been repeatedly observed and are determined to be basic characteristics of the new variety. The combination of these characteristics distinguishes this *Solenostemon* as a new and distinct variety.

BRIEF DESCRIPTION OF THE PHOTOGRAPHS

The accompanying photographic drawing shows typical foliage characteristics of 'Mos Burvet' with colors being as true as possible with an illustration of this type. The photographic drawing shows a potted plant of the new variety.

DETAILED BOTANICAL DESCRIPTION

The plant descriptions, measurements and aforementioned photographs were taken in Gilroy, Calif. in early April 2006 in a greenhouse. These plants were about 10-12 weeks old growing in a 4 inch pot.

Color references are made to The Royal Horticultural Society Colour Chart (R.H.S.) 2001.

TABLE 1

DIFFERENCES BETWEEN THE NEW VARIETY 'MOS BURVET' AND A SIMILAR VARIETY

| | 'Mos Burvet' | 'Copper' (U.S. Plant Pat. No. 14,394) |
|---|---|---|
| Foliage shape: | Ovate | Deltoid |
| Foliage margin type: | Crenate | Dentate to crenate |
| Petiole length: | Longer | Shorter |
| Petiole diameter: | Larger | Smaller |

Plant:

*Form, growth and habit.*—Annual potted or garden plant grown for its distinctive and colorful foliage; Stems strong, upright and freely branching, moderately vigorous growth habit.

*Plant height.*—26.0-28.0 cm.
*Plant width.*—40.0-45.0 cm.
*Garden performance and tolerance to weather.*—Very good.

Roots:
*Number of days to initiate roots.*—About 4 days at about 22 degrees C.
*Number of days to produce a rooted cutting.*—6-8 days at 22 degrees C.
*Type.*—Fine, fibrous, free branching.
*Color.*—RHS N155B but whiter.

Foliage:
*Arrangement.*—Opposite, simple.
*Immature, leaf color, upper surface.*—Darker than RHS 187B with closest to RHS N144A margins.
*Lower surface.*—RHS 147C but a little more green with RHS 144C margins.
*Mature, leaf color, upper surface.*—Darker than RHS 187B with closest to RHS N144A margins.
*Lower surface.*—RHS 147C but a little more green with RHS 144C margins.
*Length.*—10-13 cm.
*Width.*—6.5-8.5 cm.
*Shape.*—Ovate.
*Base shape.*—Attenuate.
*Apex shape.*—Acuminate to acute.
*Margin.*—Crenate.
*Texture, upper surface.*—Slightly pubescent.
*Lower surface.*—Pubescent.
*Color of veins, upper surface.*—RHS 144C to RHS 145C.
*Color of veins, lower surface.*—RHS 144C.
*Petiole color.*—RHS 144C.
*Length.*—4.5-5.0 cm.
*Diameter.*—0.4 cm.
*Texture.*—Pubescent.

Stem:
*Color of stem.*—RHS 144B with slight blotches of RHS 144D.
*Length of stem.*—19.0-23.0 cm.
*Diameter.*—0.6-1.0 cm.
*Length of internodes.*—1.5-5.0 cm.
*Texture.*—Pubescent.

Inflorescence: Flowering development was not observed on this plant to this date. Therefore also, seed development has not been observed.

Disease/pest resistance: Disease/pest resistance has not been observed on this hybrid.

What is claimed is:

1. A new and distinct variety of *Solenostemon* plant named 'Mos Burvet' substantially as illustrated and described herein.

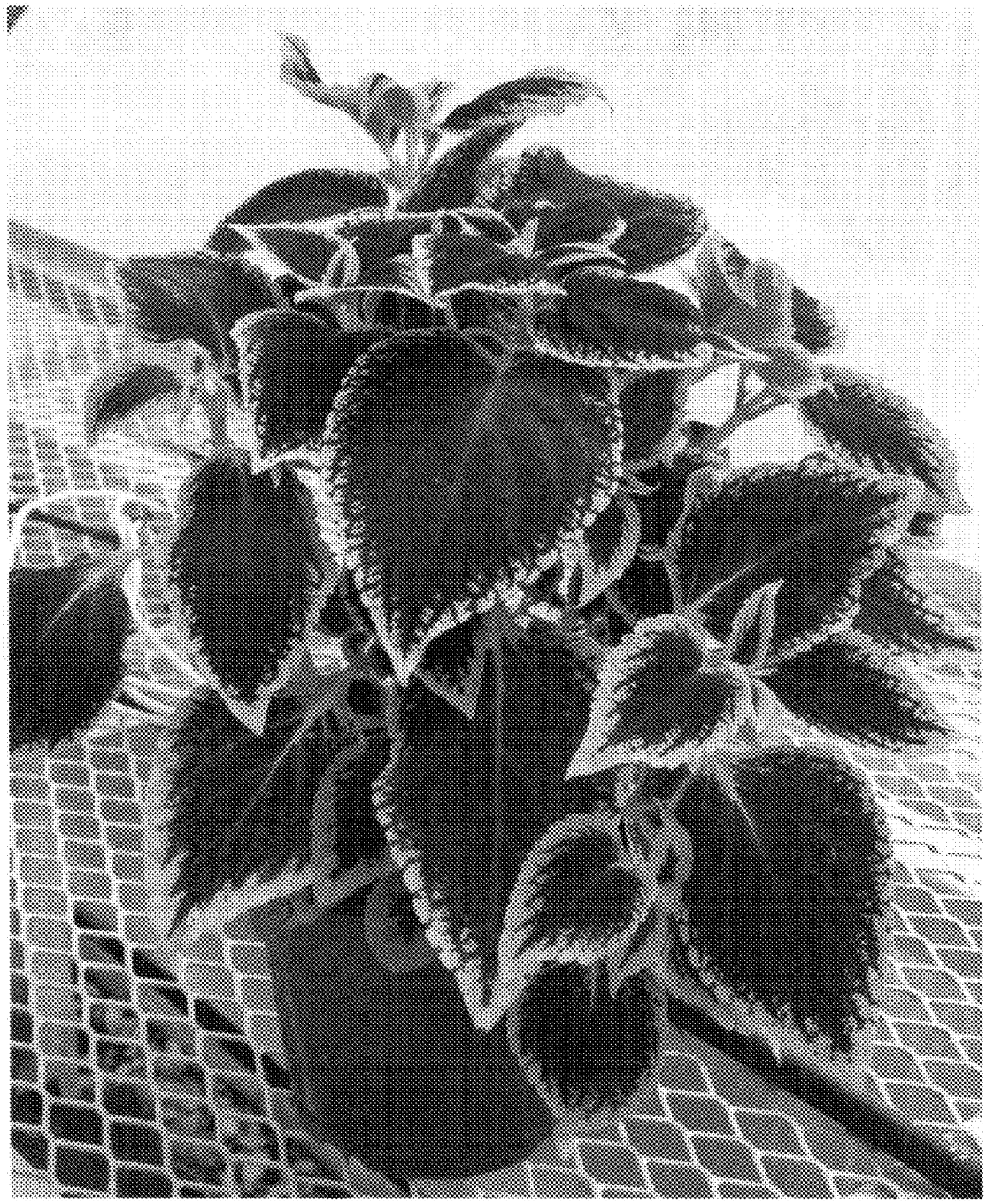

* * * * *